United States Patent
Kleiner et al.

(10) Patent No.: US 8,105,391 B2
(45) Date of Patent: Jan. 31, 2012

(54) MERHODS OF TREATMENT WITH DEVICES HAVING A COATING CONTAINING PEGYLATED HYALURONIC ACID AND A PEGYLATED NON-HYALURONIC ACID POLYMER

(75) Inventors: Lothar W. Kleiner, Los Altos, CA (US); Connie S. Kwok, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/753,034

(22) Filed: Apr. 1, 2010

(65) Prior Publication Data

US 2010/0189758 A1    Jul. 29, 2010

Related U.S. Application Data

(62) Division of application No. 11/367,561, filed on Mar. 3, 2006, now Pat. No. 7,713,637.

(51) Int. Cl.
| | |
|---|---|
| *A61F 2/02* | (2006.01) |
| *A61F 2/04* | (2006.01) |
| *A61F 2/82* | (2006.01) |
| *A61K 47/06* | (2006.01) |
| *A61K 47/22* | (2006.01) |
| *A61K 47/36* | (2006.01) |
| *A61K 24/42* | (2006.01) |

(52) U.S. Cl. ............ 623/23.57; 623/1.1; 623/1.42; 623/1.43; 623/1.46; 623/1.48; 623/1.49; 623/13.18; 623/23.58; 623/23.59; 623/23.7; 623/23.75; 424/422; 424/423; 424/426; 424/78.17; 424/78.3; 424/78.37; 424/78.38; 536/55.1; 514/54; 525/54.1; 525/54.2; 525/54.23; 525/54.3; 525/63; 525/66; 428/480; 428/522; 428/532

(58) Field of Classification Search ............ None
See application file for complete search history.

(56) References Cited

U.S. PATENT DOCUMENTS

| 6,111,014 | A | 8/2000 | Wang et al. |
|---|---|---|---|
| 6,117,947 | A | 9/2000 | Wang et al. |
| 6,258,121 | B1 | 7/2001 | Yang et al. |
| 6,368,658 | B1 | 4/2002 | Schwarz et al. |
| 6,476,156 | B1 | 11/2002 | Kim et al. |
| 6,585,765 | B1 | 7/2003 | Hossainy et al. |
| 6,632,446 | B1 | 10/2003 | Hubbell et al. |
| 6,638,538 | B1 | 10/2003 | Hashimoto et al. |
| 6,887,270 | B2 | 5/2005 | Miller et al. |
| 6,998,456 | B1 | 2/2006 | Mallapragada et al. |
| 7,063,884 | B2 | 6/2006 | Hossainy et al. |
| 7,311,980 | B1 | 12/2007 | Hossainy et al. |
| 7,329,413 | B1 | 2/2008 | Pacetti et al. |
| 7,387,810 | B2 | 6/2008 | Hossainy |
| 7,456,275 | B2 | 11/2008 | Shimoboji |
| 7,713,637 | B2 * | 5/2010 | Kleiner et al. ........... 428/522 |
| 2004/0175406 | A1 | 9/2004 | Schwarz |
| 2004/0224001 | A1 | 11/2004 | Pacetti et al. |
| 2005/0112170 | A1 | 5/2005 | Hossainy et al. |
| 2005/0123505 | A1 | 6/2005 | Chen et al. |
| 2005/0164980 | A1 | 7/2005 | Shimoboji |
| 2005/0169957 | A1 | 8/2005 | Hossainy |
| 2005/0244363 | A1 | 11/2005 | Hossainy et al. |

FOREIGN PATENT DOCUMENTS

WO    WO 2004/022603    3/2004

OTHER PUBLICATIONS

International Search Report for PCT/US2007/004558, filed Feb. 15, 2007, mailed Aug. 2, 2007, 12 pgs.

* cited by examiner

*Primary Examiner* — Vivian Chen

(74) *Attorney, Agent, or Firm* — Squire, Sanders & Dempsey (US) LLP

(57) ABSTRACT

Provided herein are a method, which comprises implanting in a patient an implantable device comprising a coating that includes a PEGylated hyaluronic acid and a PEGylated non-hyaluronic acid biocompatible polymer and the methods of use thereof.

17 Claims, No Drawings

MERHODS OF TREATMENT WITH DEVICES HAVING A COATING CONTAINING PEGYLATED HYALURONIC ACID AND A PEGYLATED NON-HYALURONIC ACID POLYMER

CROSS-REFERENCE TO RELATED APPLICATION

This is a divisional application of U.S. application Ser. No. 11/367,561, filed on Mar. 3, 2006 and issued as U.S. Pat. No. 7,713,637 on May 11, 2010, the teaching of which is incorporated herein by reference in its entirety.

BACKGROUND OF THE INVENTION

1. Field of the Invention

This invention generally relates to a coating or a medical device such as stent formed of a PEGylated hyaluronic acid (HA) and a PEGylated non-HA polymer.

2. Description of the Background

A current paradigm in the art of stenting is to use biomaterials to modulate biological responses to the implant surface. One of the biomaterials is hyaluronic acid (HA). Due to HA's hydrophilicity, it is often modified for the ease of manufacture process. One of the modification methods is to modify HA with PEG and/or adding positive charge tridodecyl methyl ammonium chloride (TDMAC) to neutralize the negative charges of HA to make the HA dissolvable in an organic solvent. However, a coating formed of such derivatized HA often lacks the mechanical properties required of the coating for an implantable device (e.g., a stent).

The present invention provides embodiments as follows to address the above-identified needs and problems.

SUMMARY OF THE INVENTION

The present invention provides a method of treating a disorder. The method comprises implanting in a patient an implantable device. The implantable device comprises a polymer blend that includes a PEGylated HA and a PEGylated non-HA polymer. The polymer defined herein can be used alone or in combination with another biocompatible polymer and/or a biobeneficial material to form coatings on implantable medical devices or to form the implantable medical devices themselves. The polymers or polymer blends described herein can also be used to form the implantable device itself. The implantable device can optionally include a bioactive agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication anastomotic proliferation for vein and artificial grafts, bile duct obstruction, ureter obstruction, tumor obstruction, or combinations thereof.

DETAILED DESCRIPTION

The present invention provides for a polymer blend that includes a PEGylated HA and a PEGylated non-HA polymer. The polymer defined herein can be used alone or in combination with another biocompatible polymer and/or a biobeneficial material to form coatings on implantable medical devices or to form the implantable medical devices themselves. The coating or device can optionally include one or more other biocompatible polymers. The coating or device can optionally include one or more biobeneficial materials. Further, the coating or device can optionally include one or more bioactive agents.

The PEGylated HA and the PEGylated non-HA polymer can be used in the ratio (PEGylated HA/PEGylated non-HA) of between about 0.01:0.99 and about 0.99:0.01, between about 0.1:0.9 and about 0.9:0.1, between about 0.2:0.0.8 and about 0.8:0.2, between about 0.3:0.7 and about 0.7:0.3, or between about 0.4:0.6 and about 0.6:0.4 or of about 0.5:0.5.

A device having a coating described herein can be used to treat, prevent, or ameliorate disorder such as atherosclerosis, thrombosis, restenosis, hemorrhage, vascular dissection or perforation, vascular aneurysm, vulnerable plaque, chronic total occlusion, claudicationanastomotic proliferation for vein and artificial grafts, bile duct obstruction, ureter obstruction, tumor obstruction, or combinations thereof.

PEGylated HA

The term hyaluronic acid (HA) includes HA molecules, fragments, and derivatives thereof. In particular, the term HA and HA fragments as used herein refers to any molecules that have a unit or repeating units as shown in Formula I:

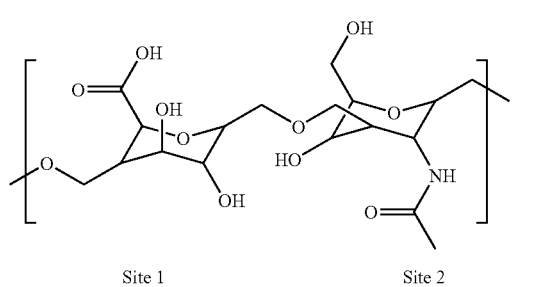

Formula I

Depending on the number of the units of Formula I present, the HA can have a weight-average molecule weight ($M_w$) in the range from about 250 Daltons to about 10,000,000 Daltons, e.g., about 500 Daltons to about 1,000,000 Daltons, about 1000 Daltons to about 500,000 Daltons, about 2,000 Daltons to about 400,000 Daltons, about 5,000 Daltons to about 300,000 Daltons, about 10,000 Daltons to about 200,000 Daltons, about 10,000 Daltons to about 100,000 Daltons, about 10,000 Daltons to about 75,000 Daltons, or about 10,000 Daltons to about 50,000 Daltons. Some embodiments specifically exclude one or more HA or HA fragments having the molecular weight ranges described herein.

As used herein, the term PEGylated refers to being modified with poly(ethylene glycol) (PEG) or a molecule of the similar nature via a covalent bond or non-covalent force such as ionic interaction or hydrogen bonding. Molecules similar to PEG in nature include, but are not limited to, poly(olefin glycol) such as polypropylene glycol, poly(olefin oxide) such as poly(ethylene oxide or polypropylene oxide), or a copolymer having a PEG block, a poly(olefin glycol) block, and/or a poly(olefin oxide) block such as PLURONIC™ surfactants (polypropylene oxide-co-polyethylene glycol) or poly(tetramethylene glycol).

The PEG molecules as used herein have a weight average molecular weight ($M_w$) preferably below about 50,000 Daltons, e.g., in the range from about 100 Daltons to about 50,000 Daltons, about 150 Daltons to about 45,000 Daltons, about 300 Daltons to about 45,000 Daltons, about 500 Daltons to about 45,000 Daltons, about 750 Daltons to about 45,000 Daltons, about 1,000 Daltons to about 45,000 Daltons, about 1,500 Daltons to about 45,000 Daltons, about 3,000 Daltons to about 45,000 Daltons, about 5,000 Daltons to about 45,000 Daltons, about 7,500 Daltons to about 45,000 Daltons, about 10,000 Daltons to about 45,000 Daltons, about 15,000 Daltons to about 45,000 Daltons, about 20,000 Daltons to about 45,000 Daltons, about 25,000 Daltons to about 45,000 Daltons, about 30,000 Daltons to about 45,000 Daltons, about 35,000 Daltons to about 45,000 Daltons, about 40,000 Daltons to about 45,000 Daltons. Some embodiments specifically exclude one or more PEG molecules having the molecular weight ranges described herein.

In some embodiments, the PEGylated HA described herein can have a weight average molecular weight ($M_w$) in the range from about 250 Daltons to about 10,000,000 Daltons, e.g., about 500 Daltons to about 1,000,000 Daltons, about 1000 Daltons to about 500,000 Daltons, about 2,000 Daltons to about 400,000 Daltons, about 5,000 Daltons to about 300,000 Daltons, about 10,000 Daltons to about 200,000 Daltons, about 10,000 Daltons to about 100,000 Daltons, about 10,000 Daltons to about 75,000 Daltons, or about 10,000 Daltons to about 50,000 Daltons. In some embodiments, the PEGylated HA can have a molecular weight in the range from about 70,000 Daltons to about 320,000 Daltons. Some embodiments specifically exclude one or more PEGylated HA or HA fragments having the molecular weight ranges described herein.

PEGylated Non-HA Polymer

The term PEGylated non-HA polymer, as used herein, refers to any biocompatible polymer modified with a PEG molecule. The modification by PEG molecule of the biocompatible polymer can be in any form known in the art. For example, the PEGylated non-HA polymer can have PEG molecule in the backbone in the form of a block copolymer or random copolymer. Alternatively, the PEGylated non-HA polymer can have PEG molecules as pendant groups.

The non-HA polymer can be any biocompatible polymer commonly used in the art of medical or biomedical coating. Some examples of the non-HA polymer for forming the PEGylated non-HA polymer include, but are not limited to, poly(ester amide), polyacids, polyesters, polyhydroxyalkanoates (PHA), polycaprolactone, poly(lactide-co-caprolactone), poly(glycolide-co-caprolactone), poly(dioxanone), poly(ortho esters), poly(anhydrides), poly(tyrosine carbonates), poly(tyrosine arylates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyolefins, polyisobutylene and ethylene-alpha-olefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers, poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), copoly(ether-esters), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof. In some embodiments, the copolymer described herein can exclude any one of the aforementioned polymers.

The term PHA as used herein includes, but is not limited to, poly(2-hydroxyacids), poly(3-hydroxyacids), poly(4-hydroxyacids), and copolymers that include any of 2-hydroxyacids, 3-hydroxyacids, and/or 4-hydroxyacids. 2-hydroxyacids include, but are not limited to, lactic acid, glycolic acid and other hydroxyacids having a substituent on the second carbon position of the 2-hydroxyacid molecule. 3-Hydroxyacids include, but are not limited to, 3-hydroxypropanoic acid, 3-hydroxybutyric acid, 3-hydroxyvaleric acid, 3-hydropentanoic acid, 3-hydroxyhexanoic acid, or 3-hydroxyhepanoic acid and other hydroxyacids having a substituent on the third carbon position of the 3-hydroxyacid molecule. 4-Hydroxyacids include, but are not limited to, 4-hydroxybutyric acid, 4-hydroxyvaleric acid, 4-hydropentanoic acid, 4-hydroxyhexanoic acid, 4-hydroxyhepanoic acid, or 4-hydroxyoctanoic acid and other hydroxyacids having a substituent on the fourth carbon position of the 4-hydroxyacid molecule. Other polymers can be found in Polymeric Biomaterials, 2nd edition, Severian Dumitriu, Ed, Marcel Dekker, 2001; and Biomaterials Science, An Introduction to Materials in Medicine, Ratner, Hoffman, Schoen and Lemmons, Eds. Academic Press, New York, 1996.

The hydroxyacids provided above, other than glycolic acid, are optically active and can include the L-enantiomer, the D-enantiomer, a blend of L-enantiomer and D-enantiomer, and a racemic mixture of the L-enantiomer and the D-enantiomer thereof. For example, the term PLA includes, but are not limited to, poly(D,L-lactide), poly(L-lactide), poly(L-lactide-co-D,L-lactide), poly(D,L-lactide-co-glycolide), or poly(L-lactide-co-glycolide).

Some examples of these PEGylated non-HA polymers include acrylate or methacrylate based polymers having a general formula of

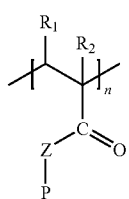

where $R_1$ and $R_2$ are independently H, methyl, ethyl, propyl, isopropyl, n-butyl, isobutyl, or phenyl, where Z is O, S, or $NR_3$ where $R_3$ is H, methyl, ethyl, propyl, isopropyl, n-butyl, isobutyl, or phenyl, where P is a PEG molecule, and where n is a positive integer ranging from 1 to 100,000.

Other examples of PEGylated non-HA polymers include PEGylated bioactive agents. Such bioactive agents or drugs can be a peptide, protein, antibody, or a drug. Examples of PEGylated proteins and peptides are PEGylated RGD peptide, PEGylated ANP peptide, PEGylated CNP peptide, and PEGylated osteopontin or combinations thereof. In some embodiments, such PEGylated bioactive agents include PEGylated Examples of PEGylated drugs include PEGylated anti-proliferatives, PEGylated inflammatories, and combinations thereof.

Other examples PEGylated non-HA polymer include, but are not limited to, e.g. poly(ethylene oxide)/poly(lactic acid) (PEO/PLA), poly(styrene-isoprene-styrene)-PEG (SIS-PEG), polystyrene-PEG, polyisobutylene-PEG, polycaprolactone-PEG (PCL-PEG), poly(lactic acid-co-PEG) (PLA-PEG), poly(methyl methacrylate)-PEG (PMMA-PEG), polydimethylsiloxane-co-PEG (PDMS-PEG), and poly(vinylidene fluoride)-PEG (PVDF-PEG).

In a preferred embodiment, the PEGylated non-HA polymer is PEGylated PLA or contains a PEGylated PLA block or moiety.

Non-HA Polymers

In some embodiments, the coating or absorbable device (e.g., absorbable stent) can optionally include one or more Non-HA polymers. The combination can be mixed, blended, or coated in separate layers. The additional biocompatible polymer can be biodegradable (both bioerodable or bioabsorbable) or nondegradable, and can be hydrophilic or hydrophobic.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanoate) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof. In some embodiments, the copolymer described herein can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), or poly(L-lactic acid-co-glycolic acid), respectively.

Biobeneficial Material

In some embodiments, a coating having the features described above can include a biobeneficial material. The biobeneficial material can be a polymeric material or non-polymeric material. The biobeneficial material is preferably non-toxic, non-antigenic and non-immunogenic. A biobeneficial material is one which enhances the biocompatibility of the coating or device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), Pluronic™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, heparin, fragments and derivatives of heparin, glycosamino glycan (GAG), GAG derivatives, polysaccharide, elastin, chitosan, alginate, silicones, POLYACTIVE™, and combinations thereof. In some embodiments, the coatings can exclude any one of the aforementioned polymers.

The term POLYACTIVE™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

Bioactive Agents

A coating described above can include any bioactive agent. The bioactive agent can be any bioactive agent, which is a therapeutic, prophylactic, or diagnostic agent. These agents can have anti-proliferative or anti-inflammatory properties or can have other properties such as antineoplastic, antiplatelet, anti-coagulant, anti-fibrin, antithrombotic, antimitotic, antibiotic, antiallergic, and antioxidant. The agents can be cytostatic agents, agents that promote the healing of the endothelium such as NO releasing or generating agents, agents that attract endothelial progenitor cells, or agents that promote the attachment, migration and proliferation of endothelial cells (e.g., natriuretic peptide such as CNP, ANP or BNP peptide or an RGD or cRGD peptide), while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antiproliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. ADRIAMYCIN® from Pharmacia & Upjohn, Peapack N.J.), and mitomycin (e.g. MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX™ (bivalirudin, Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, or combinations thereof. Examples of cytostatic substances include angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINIVIL® and PRINZIDE® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), heart valve prostheses, cerebrospinal fluid shunts, pacemaker electrodes, catheters, endocardial leads (e.g., FINELINE® and ENDOTAK®, available from Guidant Corporation, Santa Clara, Calif.), anastomotic devices (e.g., CABG anastomotic clips) and connectors, orthopedic implants such as screws, spinal implants, and electro-stimulatory devices. The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. In some embodiments, the device is a absorbable stent.

Method of Use

In accordance with embodiments of the invention, a coating subjected to the treatment of a phase inversion process described above can be used to provided controlled release of a bioactive agent from a medical device (e.g., stent) during delivery and (in the case of a stent) expansion of the device, or thereafter, at a desired rate and for a predetermined time at the implantation site.

Preferably, the medical device is a stent. The stent described herein is useful for a variety of medical procedures, including, for example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described features may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of treating or ameliorating a disorder in a patient comprising implanting in the patient an implantable device, the disorder being selected from the group consisting of atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof,
wherein the implantable device comprises a coating comprising a PEGylated hyaluronic acid (HA) and a PEGylated non-HA polymer,
wherein the PEGylated HA and the PEGylated non-HA polymer are independently modified with poly(ethylene glycol) (PEG), PEG like molecule or a combination thereof,
wherein the PEG like molecule is selected from the group consisting of polyethers, polyglycols, polyalkylene oxides, and combinations thereof;
wherein the PEGylated HA has a molecular weight in the range from about 70,000 Daltons to 320,000 Daltons, and
wherein the PEGylated non-HA polymer is selected from the group consisting of PEGylated polyacrylates, PEGylated peptides, PEGylated proteins, and combinations thereof.

2. The method of claim 1, wherein the PEG like molecule is selected from the group consisting of polyglycols, polyalkylene oxides, and combinations thereof.

3. The method of claim 1, wherein the PEGylated non-HA polymer is selected from the group consisting of PEGylated polyacrylates, PEGylated peptides, and PEGylated proteins.

4. The method of claim 1, wherein the PEGylated non-HA polymer further comprises PEGylated poly(lactic acid) (PLA).

5. The method of claim 1, wherein the PEG has a weight average molecular weight ($M_w$) below about 45,000 Daltons.

6. The method of claim 1, wherein the implantable device is a stent.

7. The method of claim 1, wherein the coating further comprises a bioactive agent.

8. The method of claim 1, wherein the coating further comprises a bioactive agent selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, and combinations thereof.

9. The method of claim 8, wherein the implantable device is a stent.

10. A method of treating or ameliorating a disorder in a patient comprising implanting in the patient an implantable device, the disorder being selected from the group consisting of atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof, wherein the implantable device comprises a coating comprising a PEGylated hyaluronic acid (HA) and a PEGylated non-HA polymer;

wherein the PEGylated HA and the PEGylated non-HA polymer are independently modified with poly(ethylene glycol) (PEG), PEG like molecule or a combination thereof;

wherein the PEGylated HA has a molecular weight in the range from about 70,000 Daltons to 320,000 Daltons;

wherein the PEG like molecule is selected from the group consisting of polyethers, polyglycols, polyalkylene oxides, and combinations thereof; and wherein the PEGylated non-HA polymer is

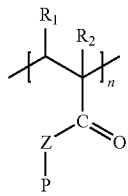

wherein $R_1$ and $R_2$ are independently H, methyl, ethyl, propyl, isopropyl, n-butyl, isobutyl, or phenyl, wherein Z is O, S, or $NR_3$ where $R_3$ is H, methyl, ethyl, propyl, isopropyl, n-butyl, isobutyl, or phenyl, wherein P is PEG or the PEG like molecule, and wherein n is a positive integer ranging from 1 to 100,000.

11. The method of claim 10, wherein the PEG like molecule is selected from the group consisting of polyglycols, polyalkylene oxides, and combinations thereof.

12. The method of claim 10, wherein the PEGylated non-HA polymer further comprises PEGylated poly(lactic acid) (PLA).

13. The method of claim 10, wherein the PEG has a weight average molecular weight ($M_w$) below about 45,000 Daltons.

14. The method of claim 10, wherein the implantable device is a stent.

15. The method of claim 10, wherein the coating further comprises a bioactive agent.

16. The method of claim 10, wherein the coating further comprises a bioactive agent selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, and combinations thereof.

17. The method of claim 16, wherein the implantable device is a stent.

* * * * *